(12) United States Patent
Brisben et al.

(10) Patent No.: US 8,565,879 B2
(45) Date of Patent: Oct. 22, 2013

(54) METHOD AND APPARATUS FOR PACING SAFETY MARGIN

(75) Inventors: Amy Jean Brisben, Saint Paul, MN (US); Shibaji Shome, Arden Hills, MN (US); Kenneth N. Hayes, Blaine, MN (US); Yanting Dong, Shoreview, MN (US); Aaron R. McCabe, Minneapolis, MN (US); Scott A. Meyer, Lakeville, MN (US); Kevin John Stalsberg, White Bear Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 139 days.

(21) Appl. No.: 13/071,680

(22) Filed: Mar. 25, 2011

(65) Prior Publication Data
US 2011/0245890 A1    Oct. 6, 2011

Related U.S. Application Data

(60) Provisional application No. 61/319,094, filed on Mar. 30, 2010.

(51) Int. Cl.
*A61N 1/08* (2006.01)

(52) U.S. Cl.
USPC .................................. 607/28; 607/27; 607/9

(58) Field of Classification Search
None
See application file for complete search history.

(56) References Cited

U.S. PATENT DOCUMENTS

| | | | |
|---|---|---|---|
| 4,979,507 A | 12/1990 | Heinz et al. | |
| 5,174,289 A | 12/1992 | Cohen | |
| 5,267,560 A | 12/1993 | Cohen | |
| 5,683,431 A | 11/1997 | Wang | |
| 5,718,720 A | 2/1998 | Prutchi et al. | |
| 6,044,296 A | 3/2000 | Zhu et al. | |
| 6,061,594 A | 5/2000 | Zhu et al. | |
| 6,169,921 B1 | 1/2001 | KenKnight et al. | |
| 6,389,316 B1 | 5/2002 | Bornzin et al. | |
| 6,408,210 B1 | 6/2002 | Bornzin et al. | |
| 6,456,879 B1 | 9/2002 | Weinberg | |
| 6,456,882 B1 | 9/2002 | Schloss | |
| 6,473,649 B1 | 10/2002 | Gryzwa et al. | |
| 6,549,806 B1 | 4/2003 | Kroll | |
| 6,564,100 B2 | 5/2003 | Warren et al. | |
| 6,615,082 B1 | 9/2003 | Mandell | |
| 6,618,621 B1 | 9/2003 | Holmstrom | |
| 6,714,819 B1 * | 3/2004 | Sloman ........................ | 607/28 |
| 6,721,601 B1 | 4/2004 | Bornzin et al. | |
| 6,731,985 B2 | 5/2004 | Poore et al. | |
| 6,738,668 B1 | 5/2004 | Mouchawar et al. | |

(Continued)

*Primary Examiner* — Jennifer Pitrak McDonald
*Assistant Examiner* — Ankit Tejani
(74) *Attorney, Agent, or Firm* — Schwegman Lundberg & Woessner, P.A.

(57) ABSTRACT

An apparatus comprises a cardiac signal sensing circuit, a pacing therapy circuit, and a controller circuit. The controller circuit includes a safety margin calculation circuit. The controller circuit initiates delivery of pacing stimulation energy to the heart using a first energy level, changes the energy level by at least one of: a) increasing the energy from the first energy level until detecting that the pacing stimulation energy induces stable capture, or b) reducing the energy from the first energy level until detecting that the stimulation energy fails to induce capture, and continues changing the stimulation energy level until confirming stable capture or the failure of capture. The safety margin calculation circuit calculates a safety margin of pacing stimulation energy using at least one of a determined stability of a parameter associated with evoked response and a determined range of energy levels corresponding to stable capture or intermittent failure of capture.

11 Claims, 11 Drawing Sheets

(56) References Cited

U.S. PATENT DOCUMENTS

| | | |
|---|---|---|
| 6,925,471 B2 | 8/2005 | Bodin et al. |
| 6,934,587 B1 | 8/2005 | Bornzin et al. |
| 7,016,732 B2 | 3/2006 | Warren et al. |
| 7,062,327 B2 | 6/2006 | Bradley et al. |
| 7,092,756 B2 | 8/2006 | Zhang et al. |
| 7,158,531 B2 | 1/2007 | Barton |
| 7,158,831 B2 | 1/2007 | Zhu |
| 7,181,280 B1 | 2/2007 | Sloman |
| 7,299,094 B1 | 11/2007 | Simon et al. |
| 7,471,983 B2 | 12/2008 | Voegele et al. |
| 7,512,441 B2 | 3/2009 | Zhang et al. |
| 7,680,536 B2 | 3/2010 | Sathaye et al. |
| 2006/0149328 A1* | 7/2006 | Parikh et al. .................... 607/28 |
| 2006/0224205 A1 | 10/2006 | Yerich et al. |
| 2006/0247691 A1 | 11/2006 | Meyer et al. |
| 2006/0247696 A1 | 11/2006 | Stalsberg et al. |
| 2006/0293717 A1 | 12/2006 | Sathaye et al. |
| 2007/0021793 A1 | 1/2007 | Voegele et al. |
| 2008/0004669 A1 | 1/2008 | Sathaye et al. |
| 2008/0039904 A1* | 2/2008 | Bulkes et al. .................... 607/62 |
| 2008/0046019 A1 | 2/2008 | Sathaye et al. |
| 2008/0221640 A1* | 9/2008 | Overstreet et al. ............... 607/48 |
| 2008/0243201 A1* | 10/2008 | Bocek et al. ...................... 607/4 |
| 2008/0288013 A1* | 11/2008 | Schecter ......................... 607/23 |
| 2009/0043351 A1 | 2/2009 | Sathaye et al. |
| 2009/0105780 A1 | 4/2009 | Voegele et al. |
| 2009/0187228 A1 | 7/2009 | Zhang et al. |

* cited by examiner

METHOD AND APPARATUS FOR PACING SAFETY MARGIN

CROSS-REFERENCE TO RELATED APPLICATIONS

This application claims the benefit of U.S. Provisional Application No. 61/319,094, filed on Mar. 30, 2010, under 35 U.S.C. §119(e), which is incorporated herein by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

Some IMDs detect events by monitoring electrical heart activity signals. In CFM devices, these events can include heart chamber expansions or contractions. By monitoring cardiac signals indicative of expansions or contractions, IMDs can detect abnormally slow heart rate, or bradycardia. In response to an abnormally slow heart rate some CFM devices deliver electrical pacing stimulation energy to induce cardiac depolarization and contraction (sometimes called capture of the heart). The stimulation energy is delivered to provide a depolarization rate that improves hemodynamic function of the patient. It is desirable to optimize the pacing stimulation energy delivered when pacing the heart to ensure therapy delivery and yet avoid stressing the heart unnecessarily and compromising battery life.

OVERVIEW

This document relates generally to systems, devices, and methods that provide electrical pacing therapy to the heart of a patient or subject. In particular it relates to, systems, devices, and methods that determine a pacing capture threshold of the heart of a patient or subject.

In example 1, an apparatus includes a cardiac signal sensing circuit configured to provide an electrical cardiac signal representative of cardiac activity of a subject, a therapy circuit configured to deliver electrical pacing stimulation energy to a heart of a subject, and a controller circuit communicatively coupled to the cardiac signal sensing circuit and the therapy circuit, and including a capture detection circuit configured to detect cardiac capture. The controller circuit is configured to initiate delivery of pacing stimulation energy to the heart using a first energy level, change the stimulation energy level by at least one of: a) increasing the stimulation energy from the first energy level until detecting that the pacing stimulation energy induces stable capture, or b) reducing the stimulation energy from the first energy level until detecting that the stimulation energy fails to induce cardiac capture, and continue the changing of the stimulation energy level until confirming the stable capture or the failure to induce capture. The controller circuit includes a safety margin calculation circuit configured to calculate a safety margin of pacing stimulation energy using at least one of a determined stability of a parameter associated with evoked response, and a determined range of energy levels corresponding to intermittent failure to induce capture.

In example 2, the controller circuit of example 1 is optionally configured to measure the evoked response parameter during the delivery of the stimulation energy and induced capture. The safety margin calculation circuit is optionally configured to categorize parameter measurements into specified ranges of parameter values, determine stability of the evoked response parameter by identifying the range of values that includes the largest number of parameter measurements, identify the smallest pacing stimulation energy that induced capture resulting in a measured parameter in the identified range, and calculate the safety margin using the identified smallest stimulation energy.

In example 3, the controller circuit of any one of examples 1 and 2 is optionally configured to measure the parameter during delivery of the stimulation energy and induced capture. The safety margin calculation circuit is optionally configured to determine stability of the evoked response parameter by specifying a range of values of the evoked response parameter, identify a largest stimulation energy resulting in a measured parameter value outside the specified range of parameter values, and calculate the safety margin using the identified largest stimulation energy.

In example 4, the evoked response parameter of any one of examples 1-3 optionally includes at least one of a peak amplitude of the evoked response, a time between delivery of pacing stimulation energy and occurrence of the peak amplitude of the evoked response, a time between delivery of pacing stimulation energy and occurrence of a zero-crossing of the amplitude of the evoked response, a polarity of a detected T-wave associated with the evoked response, a positive slope of a sensed cardiac signal that includes the evoked response, and a negative slope of a sensed cardiac signal that includes the evoked response.

In example 5, the apparatus of any one of examples 1-4 optionally includes a cardiac impedance sensing circuit communicatively coupled to the controller circuit and configured to provide a signal representative of cardiac impedance. The evoked response parameter optionally includes at least one of a near-DC value of the cardiac impedance signal, the peak-to-peak amplitude of the cardiac impedance signal, and the zero-to-peak amplitude of the cardiac impedance signal.

In example 6, the apparatus of any one of examples 1-5 optionally includes a heart sound sensor configured to provide a signal representative of mechanical activity of the heart and the evoked response parameter optionally includes at least one of a measured amplitude of a heart sound associated with evoked response, a time of occurrence of a heart sound associated with evoked response, and a power of a heart sound associated with the evoked response. The apparatus optionally may include a pulmonary pressure sensor configured to provide a signal representative of pulmonary pressure and the evoked response parameter optionally includes pulmonary pressure.

In example 7, the safety margin circuit of any one of examples 1-6 is optionally configured to calculate the safety margin using the range of energy levels corresponding to intermittent failure to induce capture. The safety margin is optionally calculated as the energy level of the stimulation energy corresponding to stable capture plus a specified stimulation energy increment value minus the energy level corresponding to confirmed capture when stimulation energy corresponding to the stable capture is different from the stimulation energy corresponding to confirmed capture. Otherwise a specified minimum increment of stimulation energy is used as the safety margin.

In example 8, the safety margin circuit of any one of examples 1-7 is optionally configured to calculate the safety margin using the range of energy levels corresponding to intermittent failure to induce capture. The safety margin is optionally calculated as the difference between the energy level immediately prior to first detecting loss of capture and the energy level immediately prior to confirming loss of capture when a stimulation energy level corresponding to the confirmed loss of capture is different from the stimulation energy corresponding to the first detected loss of capture. Otherwise a specified minimum increment of stimulation energy is used as the safety margin.

In example 9, the apparatus of any one of examples 1-8 optionally includes a memory circuit integral to or communicatively coupled to the controller circuit. The safety margin calculation circuit is optionally configured to trend pacing stimulation energy thresholds that induce an evoked response and trend calculated safety margins. The controller circuit is optionally configured to determine a pacing stimulation energy using a trended pacing stimulation energy threshold and a trended calculated safety margin.

In example 10, the therapy circuit of any one of examples 1-9 is optionally configured to deliver pacing stimulation energy to the heart using a plurality of pacing vectors. The safety margin calculation circuit is optionally configured to calculate a safety margin for at least a portion of the plurality of the pacing vectors. The controller circuit is optionally configured to select a pacing vector for delivering pacing stimulation energy using the calculated safety margins.

In example 11, the controller circuit of any one of examples 1-10 is optionally configured to identify candidate pacing vectors for delivering pacing stimulation energy to a heart chamber, receive a parameter measurement from a hemodynamic function circuit, wherein the parameter measurement indicates hemodynamic function of pacing for at least a portion of the identified candidate vectors, determine a pacing stimulation energy threshold that induces an evoked response for the portion of the identified candidate vectors, determine a phrenic nerve stimulation threshold for the portion of the identified candidate vectors, calculate a pacing stimulation energy for a candidate vector using its calculated safety margin, and select a pacing vector from among the candidate vectors according to its measured hemodynamic function parameter and a difference between its measured phrenic nerve stimulation threshold and its calculated pacing stimulation energy.

In example 12, a method includes delivering pacing stimulation energy to a heart of a subject using a medical device, wherein the stimulation energy includes a first energy level, changing the stimulation energy level by at least one of: a) increasing the stimulation energy from the first energy level until detecting that the pacing stimulation energy induces cardiac capture, or b) reducing the stimulation energy from the first energy level until detecting that the stimulation energy fails to induce cardiac capture, continuing the changing of the stimulation energy level until confirming the inducement of stable capture or the failure to induce capture, and calculating, with the medical device, a safety margin of pacing stimulation energy using at least one of a determined stability of a parameter associated with evoked response, and a range of energy levels corresponding to intermittent failure to induce capture.

In example 13, stability of the evoked response parameter of example 12 is optionally determined by measuring the parameter during the delivery of the stimulation energy and induced capture, grouping parameter measurements into specified ranges of values, identifying the range of values that includes the largest number of parameter measurements, and identifying the smallest stimulation energy that induced evoked response resulting in a measured parameter in the identified range. The calculating a safety margin optionally includes calculating the safety margin using the identified smallest stimulation energy.

In example 14, stability of the evoked response parameter of any one of examples 12 and 13 is optionally determined by specifying a range of parameter values, measuring the parameter during delivery of the stimulation energy and induced capture, and identifying a largest stimulation energy resulting in a measured parameter value outside the specified range of parameter values. The calculating a safety margin optionally includes calculating the safety margin using the identified largest stimulation energy.

In example 15, the evoked response parameter of any one of examples 12-14 optionally includes at least one of a time between delivery of pacing stimulation energy and occurrence of the peak amplitude of the evoked response, the peak amplitude of the evoked response, a time between delivery of pacing stimulation energy and occurrence of a zero-crossing of the amplitude of the evoked response, a polarity of a detected T-wave associated with the evoked response, a positive slope of a sensed cardiac signal that includes the evoked response, a negative slope of a sensed cardiac signal that includes the evoked response, a DC or near-DC cardiac impedance value, amplitude of cardiac impedance, the amplitude of a heart sound associated with evoked response, a time of occurrence of a heart sound associated with evoked response, a power of a heart sound associated with evoked response, and pulmonary pressure.

In example 16, the method of any one of examples 12-15 optionally includes calculating the safety margin using a range of energy levels corresponding to intermittent failure to induce capture. The safety margin is optionally calculated as the energy level of the stimulation energy corresponding to the stable capture plus a specified stimulation energy increment value minus the energy level corresponding to the confirmed capture when stimulation energy corresponding to the stable capture is different from the stimulation energy corresponding to confirmed capture. Otherwise a specified minimum increment of stimulation energy is used as the safety margin.

In example 17, the method of any one of examples 12-16 optionally includes calculating the safety margin using a range of energy levels corresponding to intermittent failure to induce capture. A safety margin of pacing stimulation energy is optionally calculated as the difference between the energy level immediately prior to detecting loss of capture and the energy level immediately prior to confirming loss of capture when a stimulation energy level corresponding to the confirmed loss of capture is different from the stimulation energy corresponding to the first loss of capture. Otherwise a specified minimum increment of stimulation energy is used as the safety margin.

In example 18, the method of any one of examples 12-17 optionally includes trending a pacing stimulation energy threshold that induces capture, trending the calculated safety margin, and determining a pacing stimulation energy using the trended pacing stimulation energy and the trended calculated safety margin.

In example 19, the method of any one of examples 12-18 optionally includes using the calculated safety margin to determine a pacing vector for delivering pacing stimulation energy to the heart.

In example 20, the determining a pacing vector for delivering pacing stimulation energy to the heart of example 19 optionally includes identifying candidate vectors for delivering the pacing stimulation energy, measuring a parameter indicating hemodynamic function of pacing for at least a portion of the identified candidate vectors, measuring a pacing stimulation energy threshold that induces capture for the portion of the identified candidate vectors, measuring a phrenic nerve stimulation threshold for the portion of the identified candidate vectors, calculating a pacing stimulation energy for a candidate vector using its calculated safety margin, and identifying a preferred vector from among the candidate vectors according to its measured hemodynamic function parameter and a difference between its measured phrenic nerve stimulation threshold and its calculated pacing stimulation energy.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

An implantable medical device (IMD) may include one or more of the features, structures, methods, or combinations thereof described herein. For example, a cardiac monitor or a cardiac stimulator may be implemented to include one or more of the advantageous features or processes described below. It is intended that such a monitor, stimulator, or other implantable or partially implantable device need not include all of the features described herein, but may be implemented to include selected features that provide for unique structures or functionality. Such a device may be implemented to provide a variety of therapeutic or diagnostic functions.

As explained above, pacing stimulation energy should be optimized for a patient. If the pacing energy is too high, the stimulation may cause stress on the heart and the battery life of an implanted device will be needlessly short. If the pacing stimulation energy is too low, the pacing energy will not evoke a response in the heart (i.e., will not induce capture of the heart, which is a cardiac depolarization that results in contraction). Tests can be run by IMDs to determine an optimum energy threshold for pacing therapy. The optimum threshold is the minimum level of stimulus energy that will induce capture in excitable cardiac tissue. In other words, the tests automatically try to find the minimum electrical stimulation required to consistently cause a cardiac depolarization. The optimum threshold may vary over time for a patient due to maturation of myocardial tissue around an implanted electrode, drug therapy prescribed to the patient, an episode of myocardial infarction, and defibrillation of the myocardial tissue. Therefore, the tests are run more than once by a device while the device is implanted.

When an optimum pacing threshold is found, pacing stimulation output of a CFM device is set by typically adding a safety margin to the determined threshold. Pacing threshold can be expressed in terms of voltage or current, pacing pulse duration, or energy level. The safety margin may be a fixed increment (e.g., adding one volt) added to the threshold voltage level, or may be a specified multiple of the pacing threshold (e.g., doubling the determined pacing threshold). Instead of increasing a pacing threshold using a standard safety margin, it would be desirable to optimize both the safety margin and the pacing threshold for the patient. The optimized safety margin may result in reduced stress on the heart and additional battery savings for the medical device.

Figure 1:
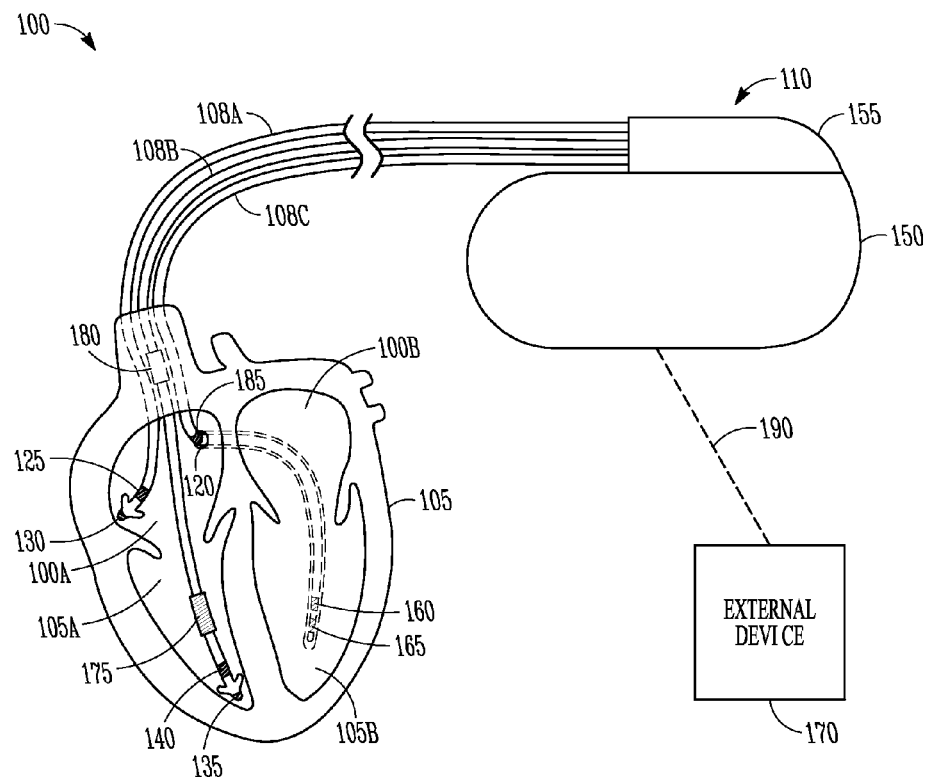
FIG. 1 is an illustration of an example of portions of a system that includes an IMD.

FIG. 1 is an illustration of portions of a system that uses an IMD 110. Examples of IMD 110 include, without limitation, a pacer, a defibrillator, a cardiac resynchronization therapy (CRT) device, or a combination of such devices. The system 100 also typically includes an IMD programmer or other external device 170 that communicates wireless signals 190 with the IMD 110, such as by using radio frequency (RF) or other telemetry signals.

The IMD 110 is coupled by one or more leads 108A-C to heart 105. Cardiac leads 108A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals.

Heart 105 includes a right atrium 100A, a left atrium 100B, a right ventricle 105A, a left ventricle 105B, and a coronary sinus 120 extending from right atrium 100A. Right atrial (RA) lead 108A includes electrodes (electrical contacts, such as ring electrode 125 and tip electrode 130) disposed in an atrium 100A of heart 105 for sensing signals, or delivering pacing therapy, or both, to the atrium 100A.

Right ventricular (RV) lead 108B includes one or more electrodes, such as tip electrode 135 and ring electrode 140, for sensing signals, delivering pacing therapy, or both sensing signals and delivering pacing therapy. Lead 108B optionally also includes additional electrodes, such as for delivering atrial cardioversion, atrial defibrillation, ventricular cardioversion, ventricular defibrillation, or combinations thereof to heart 105. Such electrodes typically have larger surface areas than pacing electrodes in order to handle the larger energies involved in defibrillation. Lead 108B optionally provides resynchronization therapy to the heart 105. Resynchronization therapy is typically delivered to the ventricles in order to better synchronize the timing of depolarizations between ventricles.

The IMD 110 may include a third cardiac lead 108C attached to the IMD 110 through the header 155. The third cardiac lead 108C includes electrodes 160 and 165 placed in a coronary vein lying epicardially on the left ventricle (LV) 105B via the coronary vein. The third cardiac lead 108C may include a ring electrode 185 positioned near the coronary sinus (CS) 120.

Lead 108B may include a first defibrillation coil electrode 175 located proximal to tip and ring electrodes 135, 140 for placement in a right ventricle, and a second defibrillation coil electrode 180 located proximal to the first defibrillation coil 175, tip electrode 135, and ring electrode 140 for placement in the superior vena cava (SVC). In some examples, high-energy shock therapy is delivered from the first or RV coil 175 to the second or SVC coil 180. In some examples, the SVC coil 180 is electrically tied to an electrode formed on the hermetically-sealed IMD housing or can 150. This improves defibrillation by delivering current from the RV coil 175 more uniformly over the ventricular myocardium. In some examples, the therapy is delivered from the RV coil 175 only to the electrode formed on the IMD can 150. In some examples, the coil electrodes 175, 180 are used in combination with other electrodes for sensing signals.

Note that although a specific arrangement of leads and electrodes are shown the illustration, the present methods and systems will work in a variety of configurations and with a variety of electrodes. Other forms of electrodes include meshes and patches which may be applied to portions of heart 105 or which may be implanted in other areas of the body to help "steer" electrical currents produced by IMD 110.

An IMD may be configured with a variety of electrode arrangements, including transvenous, endocardial, and epicardial electrodes (i.e., intrathoracic electrodes), and/or subcutaneous, non-intrathoracic electrodes, including can, header, and indifferent electrodes, and subcutaneous array or lead electrodes (i.e., non-intrathoracic electrodes).

Figure 2:
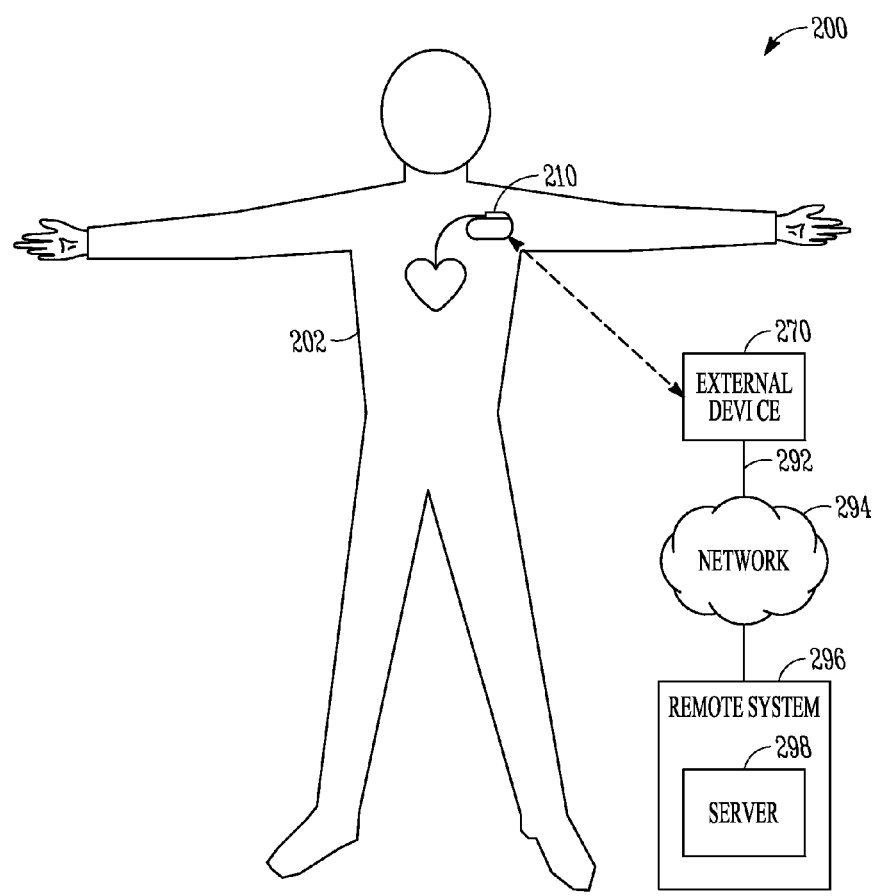
FIG. 2 is an illustration of portions of another system that uses an IMD.

FIG. 2 is an illustration of portions of another system 200 that uses an IMD 210 to provide a therapy to a patient 202. The system 200 typically includes an external device 270 that communicates with a remote system 296 via a network 294. The network 294 can be a communication network such as a phone network or a computer network (e.g., the internet). In some examples, the external device includes a repeater and communicated via the network using a link 292 that may be wired or wireless. In some examples, the remote system 296 provides patient management functions and may include one or more servers 298 to perform the functions.

Medical device based tests can be performed to automatically determine a pacing threshold for the patient. To determine appropriate pacing stimulation energy, the device delivers a sequence of pacing pulses to the heart. The sequence may include a successive reduction of the energy of the pacing pulses. A first pacing pulse that will likely induce capture is delivered. The energy of subsequent pacing pulses is reduced in steps until the device verifies that failure to induce capture has occurred. Alternatively, the sequence may include increasing the energy of the pacing pulses. A first pacing pulse that is below a threshold likely to induce capture is delivered. The energy of subsequent pacing pulses is increased in steps until the device verifies that capture was induced. The device uses information obtained from the threshold test to recommend a pacing output setting or to automatically adjust a pacing output setting. An approach for an automatic capture threshold test can be found in Sathaye et al., "Capture Detection with Cross Chamber Backup Pacing," U.S. Patent Pub. No. US 2008/0071319, filed Sep. 14, 2006, which is incorporated herein by reference in its entirety. Information obtained from the threshold test can also be used to optimize the pacing safety margin.

Figure 3:
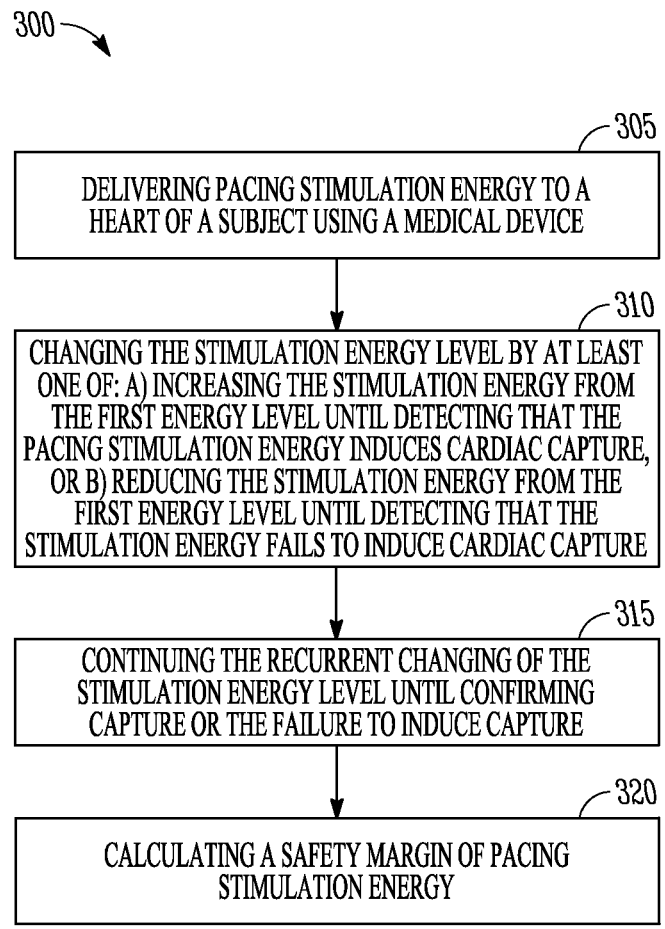
FIG. 3 is a flow diagram of an example of a method of determining a pacing safety margin.

FIG. 3 is a flow diagram of an example of a method 300 of determining a pacing safety margin. At block 305, pacing stimulation energy is delivered to a heart of a subject using a medical device, wherein the stimulation energy includes a first energy level.

At block 310, the pacing stimulation energy is then changed. In some examples, the first energy is selected to induce capture of the heart. The subsequent stimulation energy is reduced from the first energy level until detecting that the stimulation energy fails to induce cardiac capture. In certain examples, the pacing pulses are delivered in a sequence in which the pacing energy is stepped down until the pulses fail to induce capture. In some examples, the first energy level is selected to not induce capture of the heart. Subsequent stimulation energy is increased from the first energy level until detecting that the stimulation energy induces cardiac capture. In certain examples, the pacing pulses are delivered in a sequence in which the pacing energy is stepped up until the pulses induce capture.

At block 315, once the failure to induce capture is detected (e.g., in a step down test) or the inducement of capture is detected (e.g., in a step up test), the changing of the stimulation energy level is continued until confirming the inducement of capture or the failure to induce capture. In a step up test, "confirming capture" can mean that the test continues to step up at energy levels higher than the pacing threshold in order to confirm that capture is stable. In some examples, pacing stimulation energy is both decreased and increased during the test. For instance, a test may include N steps of increasing voltage and M steps of decreasing voltage during the test, where N and M are integers greater than one. This may be useful to characterize the "grey area" between definitely being above the pacing threshold and definitely being below the pacing threshold.

At block 320, a safety margin of pacing stimulation energy is calculated when loss of capture (or capture) is confirmed. In some examples, the safety margin is calculated by the medical device using a range of energy levels corresponding to intermittent inducement of capture or intermittent failure to induce capture. In either case, the safety margin can be the range of energy above threshold, indicating the range between confirmed capture and stable capture.

Figure 4:
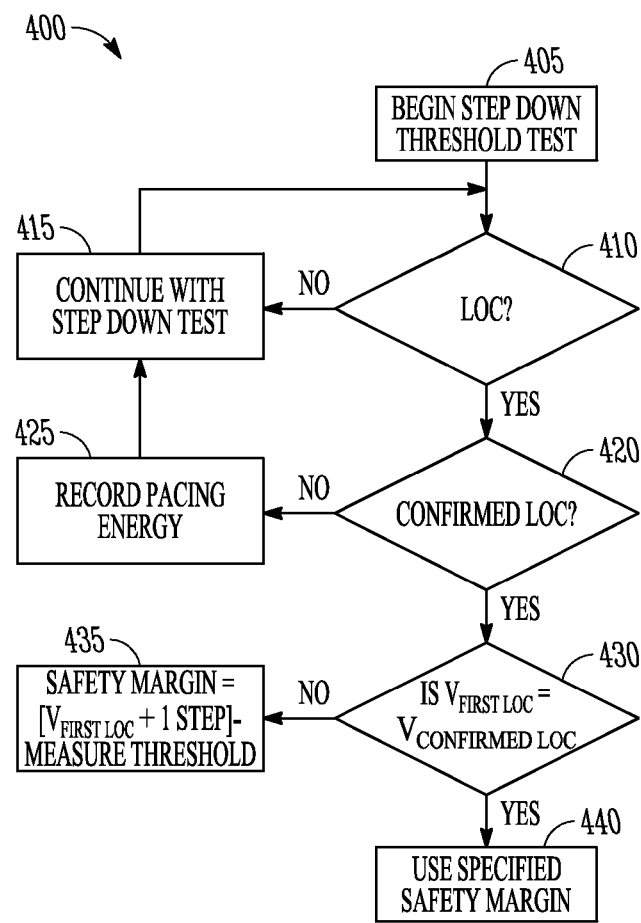
FIG. 4 is flow diagram of an example of a method of calculating a safety margin.

FIG. 4 is flow diagram of an example of a method 400 of calculating a safety margin during a step down test. At block 405, a medical device initiates a step down test. During the test, the pacing energy can be changed by one or both of stepping down the voltage of the pacing pulses and stepping down the pulse width of the pacing pulses. At block 410, the medical device determines if the pacing energy delivered resulted in loss of capture (LOC). If not the test continues at block 415.

At block 420, if the pacing energy does result in loss of capture the device tries to confirm loss of capture. Different criteria are used to declare detection of loss of capture and confirming loss of capture. Detection may be declared the first time loss of capture occurs. Confirmation may be declared when there are two occurrences of loss of capture in a row, or if there are X losses in Y pacing cycles, where X and Y are positive integers and X≤Y. If confirmation is not declared then the test continues. In some examples, the pacing voltage is recorded (e.g., stored in memory) by the device at block 425.

At block 430, if loss of capture is confirmed, it is determined if the pacing energy of the confirmation of loss of capture (e.g., $V_{confirmed\ LOC}$) is the same as the pacing threshold of the first unconfirmed detection of loss of capture (e.g., $V_{first\ LOC}$). If the pacing energy for first unconfirmed loss of capture is the same as the pacing energy for confirmed loss of capture, then there is no information from intermittent loss of capture available and a specified safety margin is used to determine pacing output. For instance, a specified minimum energy may be added to the last energy level before confirmed loss of capture, or this last energy level may be increased by a percentage (e.g., 100% or doubling the pacing energy level).

At block 435, if the pacing energy for the first unconfirmed detection of loss-of-capture is different from the pacing energy for the confirmed loss of capture then the safety margin is calculated. In some examples, the safety margin is calculated by $$\text{Safety Margin}=f[V_{first\ LOC}, \text{measured threshold, pacing energy step size, constant}] \quad (1)$$

In certain examples, pacing voltage is used to calculate the safety margin by $$\text{Safety Margin}=[V_{first\ LOC}+1\ \text{step}]-\text{measured threshold}, \quad (2)$$

where the measured threshold is the threshold immediately previous to the threshold corresponding to confirmation of loss of capture. This calculated safety margin is then added to a pacing threshold (e.g., the smallest pacing energy that consistently induced capture in the test) to determine pacing output.

Figure 5:
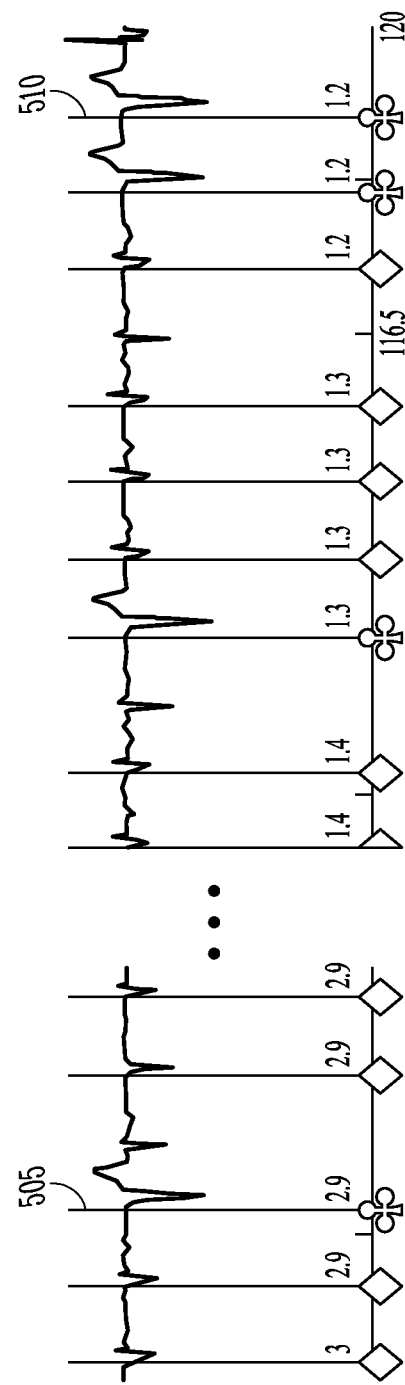
FIG. 5 shows an example of an electrocardiogram of a pacing threshold step down test.

FIG. 5 shows an example of a sensed intracardiac electrogram of a pacing threshold step down test. The example test is an LV test with an RV backup pace 80 ms after the LV pace. The test started at a voltage higher than 3 Volts (e.g., 4 or 5 Volts) and was gradually reduced until loss of capture 505 was detected at 2.9 V. The loss of capture is evident in the electrogram by the different morphology of the delayed response as compared to the morphology of the capture traces. Note that the device may pace more than once at a programmed voltage to detect loss of capture. The pacing energy was continued to be reduced until loss of capture is confirmed 510 at 1.2V. In this case loss of capture is confirmed when 2 time out paces occur within 3 cardiac cycles. In the example shown in the Figure, a safety margin can be calculated using the $V_{first\ Loc}+1$ step (=3V) and using the pacing voltage immediately previous to the threshold corresponding to confirmation of loss of capture (1.3V). Using equation (1) the calculated safety margin is 3V−1.3V=1.7V.

Figure 6:
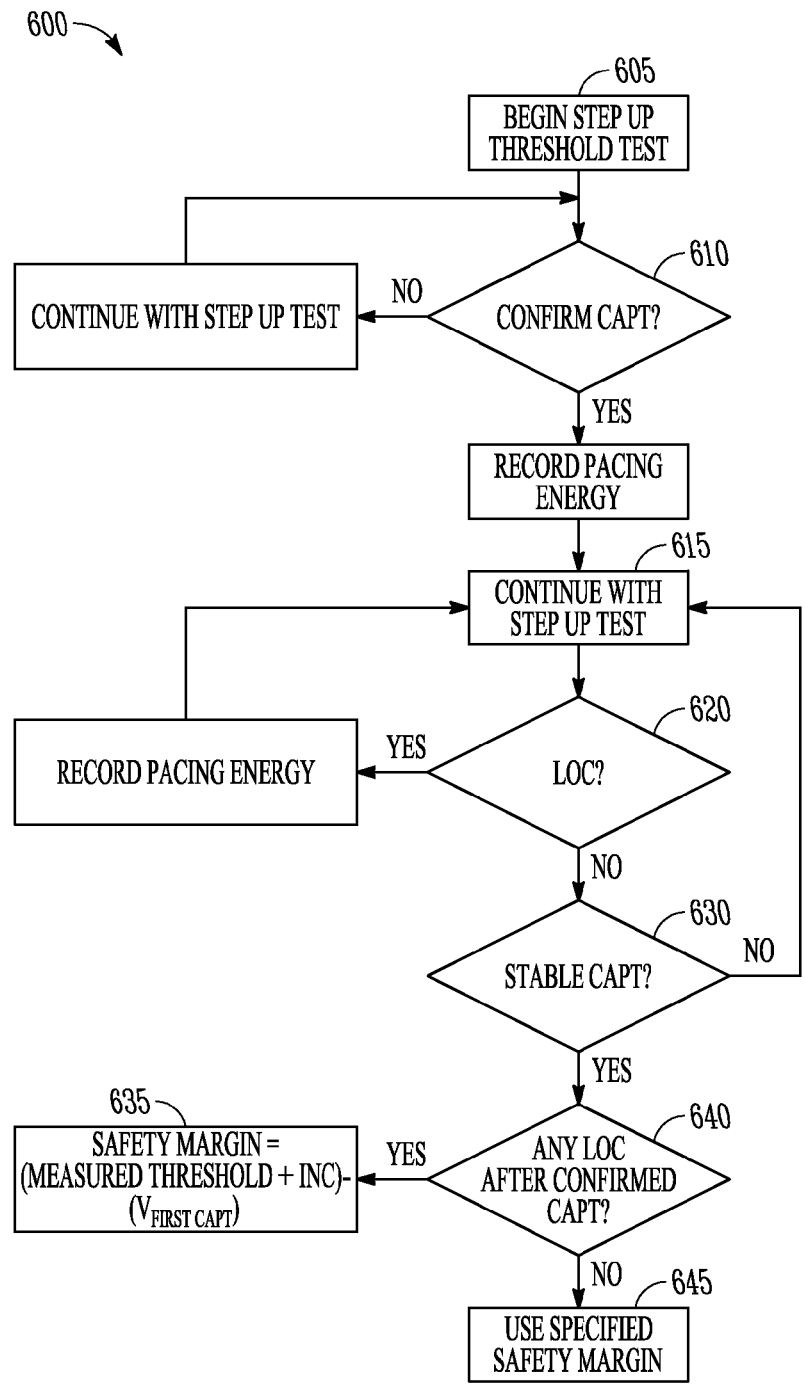
FIG. 6 is flow diagram of another example of a method of calculating a safety margin.

FIG. 6 is a flow diagram of an example of a method 600 of calculating a safety margin using a step up threshold test. At block 605, a medical device initiates a step up threshold test. The test operates similarly to the step down test except that the test may continue past confirmed capture to collect data used to calculate a safety margin.

At block 610, if capture is confirmed, the pacing energy is recorded as the threshold. The test continues at block 615 to determine the stability of the identified threshold.

At block 620, if any loss of capture events take place, pacing energy is recorded. The test continues until "stable capture" is attained. Stable capture can be defined as a pre-set energy-level (e.g., maximum pacing voltage or maximum pulse width), a rule relating to the number of identified capture beats (e.g., 6 capture without intermittent loss of capture), or a combination of energy levels and numbers of capture beats.

At block 630, if "stable" capture is confirmed, it is determined if any loss of capture beats were detected between threshold (confirmed capture) and the end of the test (stable capture) at 640. If no loss of capture events were detected, then there is no information from intermittent capture detection available and a specified safety margin is used to determine pacing output at 645.

At block 635, if any loss of capture events were detected, then the safety margin is calculated. In some examples, the safety margin is calculated by $$\text{Safety Margin}=f[V_{LOC\ events\ above\ capture}, \text{measured threshold, pacing energy step size, constant}] \quad (3)$$

In certain examples, pacing voltage is used and $$\text{Safety Margin}=[V_{largestLOC}+1\ \text{step}]-\text{measured threshold} \quad (4),$$

where the measured threshold is the threshold corresponding to confirmation of capture. In certain examples, the specified increment corresponds to a number of test steps (e.g., the voltage of one test step).

In some examples, a step up test or step down test is run multiple times to determine multiple ranges of energy levels. In certain examples, a function of the values within a range or ranges of levels can be used to determine the safety margin, such as by using a maximum, a minimum, a mean, or a median of the values, etc. In some examples, the safety margin is determined by a function of results of both step up and step down tests.

According to some examples, pacing energy is both stepped up and stepped down during a threshold test including N steps of increasing voltage and M steps of decreasing voltage during the test. If intermittent capture is evident during the test, the resulting safety margin may be calculated as a function of the largest pacing energy where loss of capture is observed during step-down, pacing energy step size, the measured pacing threshold energy, and sometimes a constant, or $$\text{Safety Margin}=f[V_{largest\ LOC}, \text{pacing energy step size, measured threshold, constant}] \quad (5).$$

In certain examples, the safety margin may be calculated as $$\text{Safety Margin}=(V_{largest\ LOC}+1\ \text{step})-\text{measured threshold}, \quad (6)$$

where measured threshold corresponds to the measured threshold of confirmed capture in the combined step-up and step down tests. Note that this is equivalent to the smallest pacing energy where capture is consistently induced minus the measured pacing threshold energy. Methods other than using intermittent pacing energy can be used to determine safety margin.

Returning to block 320 in FIG. 3, according to some examples, the safety margin is calculated by the medical device using a determined stability of a parameter associated with evoked response. In an example, the parameter related to evoked response can be the latency between the time pacing stimulation energy is delivered and the time of peak amplitude of the evoked response occurs. Determining the safety margin using stability of such a parameter results in a safety margin where evoked response is relatively stable, and is not only based on a historical or statistical metric. The safety margin can be calculated using one or both of intermittent capture/loss-of-capture and stability of evoked response parameters.

Figure 7A:
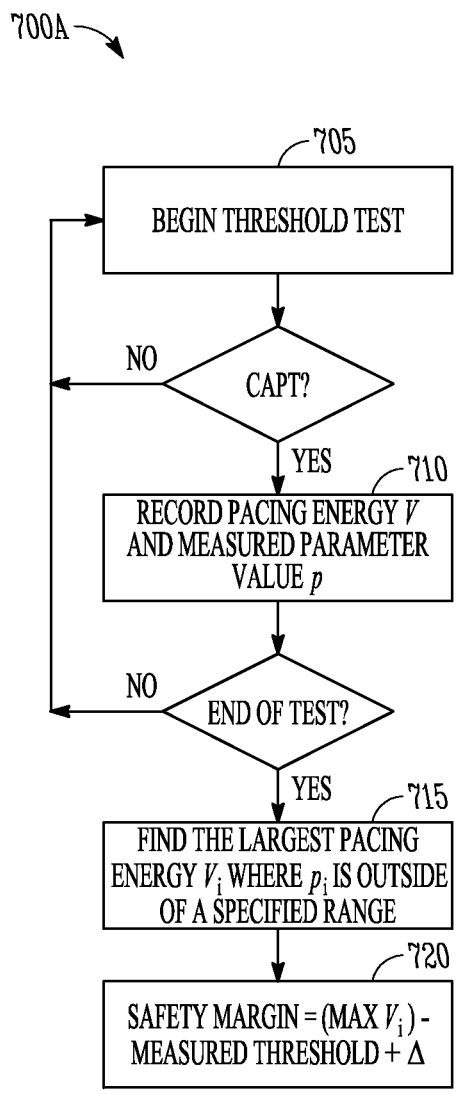
FIG. 7A is a flow diagram of still another example of a method of calculating a safety margin.

FIG. 7A is a flow diagram of another example of a method 700A of calculating a safety margin. At block 705, an automatic threshold test is executed by a medical device. If capture is detected, at block 710 the pacing energy corresponding to the capture event is recorded (e.g., stored) and a value of the parameter associated with evoked response (p) is measured during delivery of the stimulation energy and induced capture and recorded. In certain examples, the parameter is monitored during the entire auto-threshold test. In certain examples, the parameter is not monitored until capture becomes intermittent (e.g., after the first loss of capture during a step down test or after a confirmed capture during a step up test).

Prior to the test, a range of values of the parameter is specified. This range defines the stable range for the parameter and can be determined empirically, arbitrarily or by some physiologic basis. For instance, in the latency example, a clinician or other user may set the range of latency values to 15 milliseconds (ms) to 20 ms around a nominal latency value (e.g., 60 ms) when the user believes changes of 15 to 20 ms do not impact pacing efficacy.

At block 715, when the auto threshold test is completed, the largest stimulation energy ($V_i$) resulting in a measured parameter value ($p_i$) outside the specified range of parameter values is identified.

At block 720, the safety margin is then calculated using the identified largest stimulation energy. In some examples, the safety margin is calculated as a function of the identified stimulation energy ($V_i$), the measured threshold and a constant, or $$\text{Safety Margin}=f[\max V, \text{measured threshold, constant}]. \quad (7)$$

In certain examples, the safety margin is calculated using the identified stimulation energy ($V_i$) plus an increment ($\Delta$) minus the pacing stimulation threshold identified by the test, or $$\text{Safety Margin}=(\max V_i)-\text{measured threshold}+\Delta. \quad (8)$$

In some examples, the increment ($\Delta$) is equal to a test step size. In some examples, the increment is a specified minimum safety margin increment. In some examples, the increment ($\Delta$) is zero. Subsequent pacing stimulation energy can be determined by adding the calculated safety margin and the specified minimum increment of stimulation energy to a pacing stimulation energy that induced an evoked response.

Figure 8A:
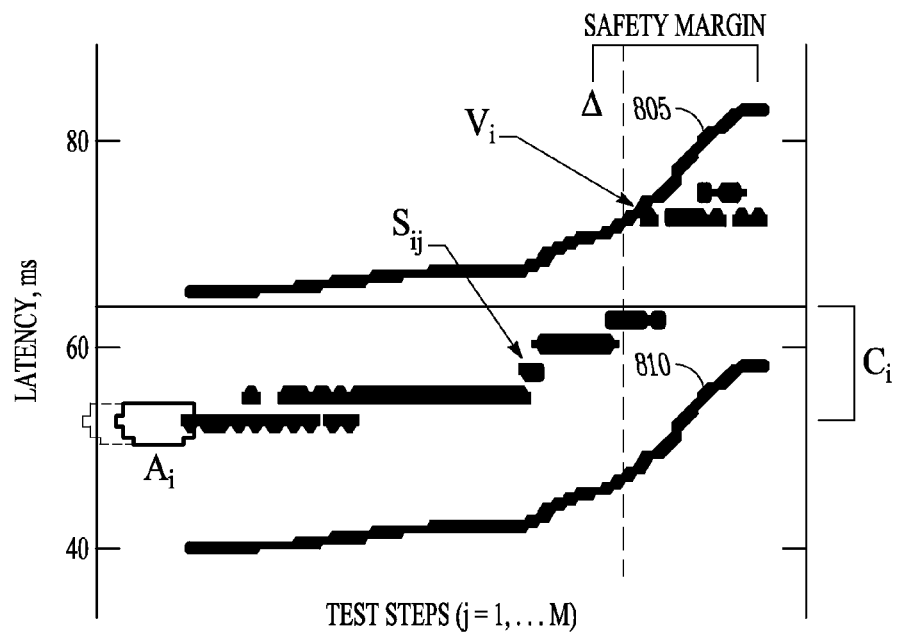
FIG. 8A illustrates an example of the method of FIG. 7A.

An example is shown in FIG. 8A. In the example, the test is a step down test, and pacing stimulation energy decreases from left to right with the test steps (j) and $s_{ij}$ indicates a test sample. The parameter of evoked response measured during the auto threshold test is the latency from the time between delivery of pacing stimulation energy and occurrence of the peak amplitude of the evoked response. Range $C_i$ is the range of latency values specified prior to the auto threshold test that defines latency stability (e.g., a range of 10 ms). The graphs 805, 810 above and below the samples indicate the limits for detection of capture. After the test the sample with the largest energy $V_i$ outside range $C_i$ is identified and the safety margin is $V_i$−threshold+$\Delta$.

Figure 7B:
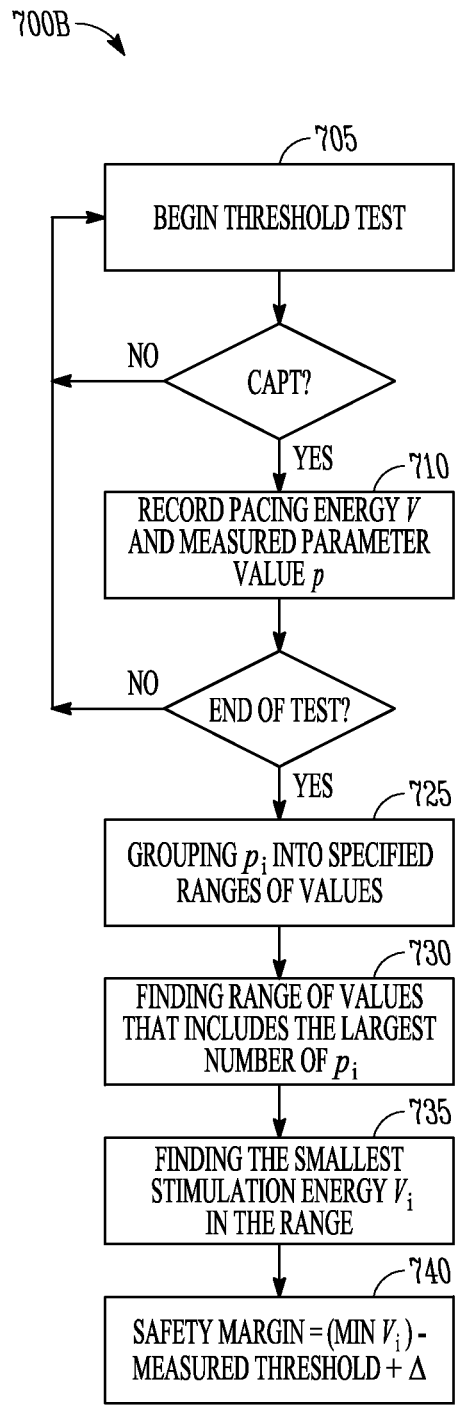
FIG. 7B is a flow diagram of still another example of a method of calculating a safety margin.

FIG. 7B is a flow diagram of another example of a method 700B of calculating a safety margin. As in the method of FIG. 7A, an automatic threshold test is executed at blocks 705 and 710. The method differs from FIG. 7A at block 725 where parameter measurements are grouped or categorized into specified ranges of values (e.g., binned into i bins $y_i$). At block 730, the range of values is identified that includes the largest number of parameter measurements. The largest bin corresponds to the pacing energy where the evoked response parameter is the most stable.

At block 735, the smallest stimulation energy $V_i$ is identified that induced evoked response resulting in a measured parameter in the identified range. At block 740, the safety margin is calculated using the identified smallest stimulation energy, or $$\text{Safety Margin}=(\min V_i)-\text{measured threshold}+\Delta. \quad (9)$$

Figure 8B:
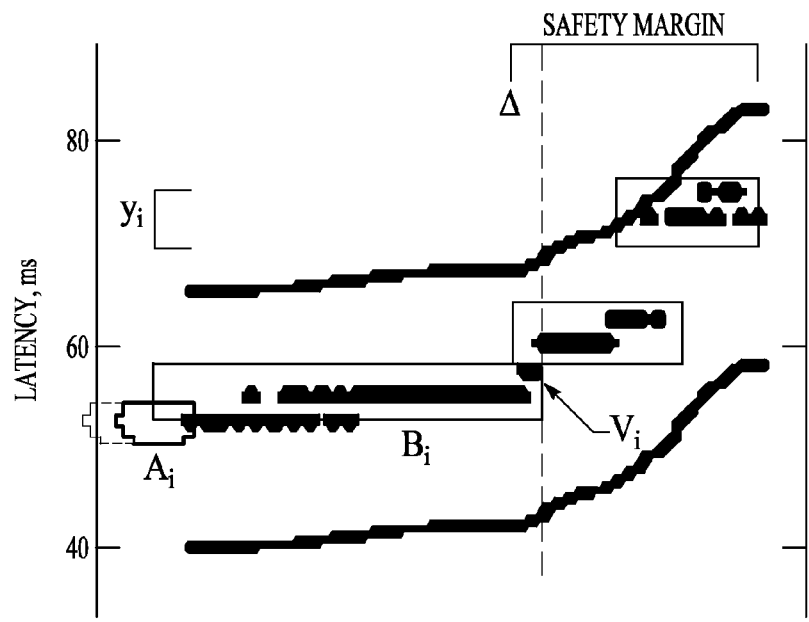
FIG. 8B illustrates an example of the method of FIG. 7B.

An example is shown in FIG. 8B. In the example, the test is a step down test, and pacing stimulation energy decreases from left to right. As in the example of FIG. 8A, the parameter of evoked response measured during the auto threshold test is latency. The parameter measurements are grouped into three bins (e.g., the bin size $y_i$=5 ms). After the test, the largest bin $B_i$ is identified. Because the test is a step down test the pacing energy for the samples decreases from left to right. Thus the right-most sample of bin $B_i$ corresponds to the smallest pacing energy $V_i$ for that bin, and the safety margin is $V_i$−threshold+$\Delta$. Again, $\Delta$ is a specified pacing energy increment value and can be equal to a test step size, a specified minimum safety margin increment, or can be zero.

A safety margin can be calculated using stability of parameters other than latency of evoked response. A non-exhaustive list of other evoked response parameters that can be used to calculate the safety margin include, the peak amplitude of the evoked response, the time between delivery of pacing stimulation energy and occurrence of a zero-crossing of the amplitude of the evoked response, a polarity of a detected T-wave associated with the evoked response, a positive slope of a sensed cardiac signal that includes the evoked response, a negative slope of a sensed cardiac signal that includes the evoked response, a near-DC cardiac impedance value, the amplitude of measured cardiac impedance, the amplitude of a heart sound associated with evoked response, a time of occurrence of a heart sound associated with evoked response, a power of a heart sound associated with evoked response, and pulmonary pressure.

Figure 9:
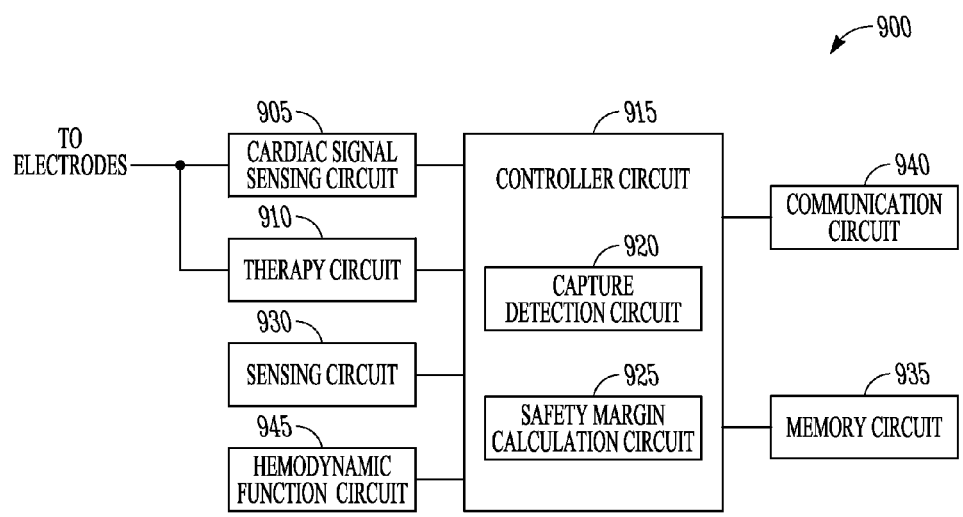
FIG. 9 is a block diagram of portions of an example of a device to determine a pacing capture threshold.

FIG. 9 is a block diagram of portions of an example of a device 900 to determine a pacing capture threshold. The device 900 includes a cardiac signal sensing circuit 905, a therapy circuit 910, and a controller circuit 915. The cardiac signal sensing circuit 905 provides an electrical cardiac signal representative of cardiac activity of a subject. In some examples, the cardiac signal sensing circuit includes one or more implantable electrodes. A sensed cardiac signal may be sampled by the device 900 to produce an intracardiac electrogram or egram. The therapy circuit 910 delivers electrical pacing stimulation energy to a heart of a subject. In some examples, the therapy circuit 910 also provides one or both of high energy cardioversion and defibrillation therapy.

The controller circuit 915 is communicatively coupled to the cardiac signal sensing circuit 905 and the therapy circuit 910. The controller circuit 915 may include a processor such as a microprocessor, a digital signal processor, application specific integrated circuit (ASIC), microprocessor, or other type of processor, interpreting or executing instructions in software or firmware. The controller circuit 915 includes other circuits or sub-circuits to perform the functions described. These circuits may include software, hardware, firmware or any combination thereof. Multiple functions can be performed in one or more of the circuits as desired.

The controller circuit 915 includes a capture detection circuit 920 to detect cardiac capture. In some examples, a first set of electrodes is used to provide the electrical pacing stimulation energy (e.g., tip electrode 135 and ring electrode 140 in FIG. 1) and a second electrode is used to detect an evoked response or capture (e.g., electrode 175 to a can electrode.) In some examples, the device 900 includes an electrode arrangement to deliver therapy and detect capture in one or more of the right ventricle (RV), the left ventricle (LV), and the right atrium (RA).

The controller circuit 915 is configured to initiate delivery of pacing stimulation energy to the heart using a first energy level and change the stimulation energy level by at least one of: a) increasing the stimulation energy from the first energy level until detecting that the pacing stimulation energy induces cardiac capture, or b) reducing the stimulation energy from the first energy level until detecting that the stimulation energy fails to induce cardiac capture. In some examples, the stimulation energy is delivered as part of an automatic threshold test. The controller circuit 915 continues the changing of the stimulation energy level until confirming the inducement of capture or the failure to induce capture, depending on whether the stimulation energy is being increased or reduced.

The controller circuit 915 also includes a safety margin calculation circuit 925 configured to calculate a safety margin of pacing stimulation energy using at least one of a determined stability of a parameter associated with evoked response and a determined range of energy levels corresponding to intermittent inducement of capture or intermittent failure to induce capture.

If the safety margin calculation circuit 925 calculates the safety margin using the range of energy levels, a confirmed capture and stable capture, or a first detected loss-of-capture and confirmed loss-of-capture, are detected as described previously.

In some examples, the controller circuit 915 increases the pacing stimulation energy during the test. When stimulation energy corresponding to the stable capture is different from the stimulation energy corresponding to confirmed capture, the safety margin is calculated as a function of the energy level of the stimulation energy corresponding to stable capture, a specified stimulation energy increment value, and the energy level corresponding to the confirmed capture (e.g., equation (3) or (4)), otherwise a specified minimum increment of stimulation energy is used as the safety margin.

In some examples, the controller circuit 915 decreases the pacing stimulation energy during the test. When a stimulation energy level corresponding to the confirmed loss of capture is different from the stimulation energy corresponding to the first detected loss of capture, the safety margin is calculated as a function of the energy level immediately prior to first detected loss of capture and the energy level immediately prior to confirmed loss of capture (e.g., equation (1) or (2)), otherwise use a specified minimum increment of stimulation energy as the safety margin.

In some examples, the controller circuit 915 both increases and decreases the pacing stimulation energy to measure intermittent pacing levels. The safety margin calculation circuit 925 may then calculate a safety margin using equation (5) or (6). In some examples, the safety margin calculation circuit 925 is configured to calculate a safety margin for pacing stimulation energy delivered to at least one of the LV, RV, and RA.

According to some examples, the safety margin calculation circuit 925 calculates the safety margin from a determined stability of a parameter associated with evoked response as described above in regard to FIGS. 7A, 7B, 8A, and 8B. The controller circuit 915 measures the evoked response parameter during the delivery of the stimulation energy and induced capture. In some examples, the safety margin calculation circuit 925 categorizes parameter measurements into specified ranges of parameter values and determines the stability of the evoked response parameter by identifying the range of values that includes the largest number of parameter measurements. The safety margin is calculated using the smallest stimulation energy that induced capture resulting in a measured parameter in the identified range (e.g., using equation (7) or (9)).

In some examples, the safety margin calculation circuit 925 determines stability of the evoked response parameter by specifying a range of values of the evoked response parameter, identifies a largest stimulation energy resulting in a measured parameter value outside the specified range of parameter values, and calculates the safety margin using the identified largest stimulation energy (e.g., using equation (7) or (8)).

In some examples, the safety margin circuit 925 determines stability of a parameter measured by the controller circuit 915 using the cardiac signal sensed by the cardiac signal sensing circuit 905. In certain examples, the controller circuit 915 measures peak amplitude of the evoked response. A cardiac signal may be sampled using an analog to digital converter (ADC) and the peak determined from the sampled values.

In certain examples, the parameter is the latency between the time pacing stimulation energy was delivered and the occurrence of the peak amplitude of the evoked response, or the occurrence of a zero-crossing of the amplitude of the evoked response. In certain examples, the parameter is a positive slope of a sensed cardiac signal that includes the evoked response (e.g., $\Delta V/\Delta t$) or a negative slope of a sensed cardiac signal that includes the evoked response (e.g., $-\Delta V/\Delta t$).

In certain examples, the parameter is the polarity of a detected T-wave associated with the evoked response. For example, T-waves can be grouped according to having a positive polarity or a negative polarity. Stability can be associated with pacing stimulation that results in long plateaus of uniform polarity, in contrast to areas where the polarity is changing back and forth from one polarity to the other.

According to some examples, the device 900 includes one or more additional sensing circuits 930 that provide a signal used to obtain the parameter associated with the evoked response. In some examples, the sensing circuit 930 includes a cardiac impedance sensing circuit communicatively coupled to the controller circuit 915. Electrodes placed within a chamber of the heart provide a signal of intracardiac impedance versus time. The impedance can be measured by providing current between two electrodes and sensing the resulting voltage across two other electrodes. Examples of possible pairs of drive electrodes and sense electrodes for an ICD are listed in Table 1 below.

TABLE 1

| | Drive Electrodes | | Sense Electrodes | |
|---|---|---|---|---|
| ICD | Drive 1 | Drive 2 | Sense 1 | Sense 2 |
| Z1 | RV tip | RV proximal | RV distal | RA ring |
| Z2 | RV distal | RV proximal | RV distal | RA ring |
| Z3 | RV distal | RV proximal | RV distal | RV proximal |
| Z4 | RV distal | Can | RV tip | Can |

Examples of possible pairs of drive electrodes and sense electrodes for a CRT device are listed below on Table 2.

TABLE 2

| CRT | Drive Electrodes | | Sense Electrodes | |
| --- | --- | --- | --- | --- |
| | Drive 1 | Drive 2 | Sense 1 | Sense 2 |
| Z1 | LV ring | RV proximal | LV tip | RA ring |
| Z2 | LV ring | RV distal | LV tip | RV tip |
| Z3 | RV distal | RV proximal | RV distal | RV proximal |
| Z4 | RV distal | Can | RV tip | Can |

Systems and methods to measure intracardiac impedance are described in Citak et al., U.S. Pat. No. 4,773,401, entitled "Physiologic Control of Pacemaker Rate Using Pre-Ejection Interval as the Controlling Parameter," filed Aug. 21, 1987, which is incorporated herein by reference in its entirety.

The evoked response parameter may include at least one of a near-DC value of the cardiac impedance signal, the peak-to-peak amplitude of the cardiac impedance signal, and the zero-to-peak amplitude of the cardiac impedance signal. In some examples, the sensing circuit 930 includes a heart sound sensor. Heart sounds are associated with mechanical vibrations from activity of a patient's heart and the flow of blood through the heart. Heart sounds recur with each cardiac cycle and are separated and classified according to the activity associated with the vibration. The first heart sound (S1) is the vibrational sound made by the heart during tensing of the mitral valve. The second heart sound (S2) marks the beginning of diastole. The third heart sound (S3) and fourth heart sound (S4) are related to filling pressures of the left ventricle during diastole. A heart sound sensor produces an electrical signal which is representative of mechanical activity of a patient's heart. An example of a heart sound sensor includes an accelerometer or microphone. An approach for measuring heart sounds can be found in Seijko et al., Method and Apparatus for Monitoring of Diastolic Hemodynamics," U.S. Pat. No. 7,115,096, filed on Dec. 30, 2002, which is incorporated herein by reference in its entirety. The evoked response parameter may include at least one of a measured amplitude of a heart sound associated with evoked response, a time of occurrence of a heart sound associated with evoked response, and a power of a heart sound associated with the evoked response.

In certain examples, the sensing circuit 930 includes an implantable pulmonary pressure sensor that provides a signal representative of pulmonary pressure. Pulmonary pressure includes the pressure within a pulmonary artery due to blood leaving the right ventricle through the pulmonary valve and going to the lungs. The evoked response parameter includes pulmonary pressure.

In some examples, the controller circuit 915 uses the calculated safety margin to set pacing output for subsequent pacing therapy, such as by using equation (2). In certain examples, the controller circuit 915 uses a safety margin increment $SM_{floor}$ of zero when determining pacing output. In some examples, the controller circuit 915 does not change the pacing output at the conclusion of a threshold test. The device 900 includes a memory circuit 935 integral to or communicatively coupled to the controller circuit 915. The controller circuit 915 may store one or both of the pacing output and the safety margin for later uploading by another device. The pacing output may be a recommended setting that is later acknowledged or confirmed by a clinician.

In some examples, the controller circuit 915 is configured to use more than one calculated safety margin when determining pacing output. The controller circuit 915 may be programmed to run a threshold test on each of several days (e.g., seven days). The controller circuit 915 then calculates a pacing output using the measured thresholds and calculated safety margin according to some function, such as $$\text{Pacing Output} = f\{\max(T_{-6}, T_{-5}, \ldots, T_0), (SM_{-6}, SM_{-5}, \ldots, SM_0), SM_{floor}\}, \quad (10)$$

where $(T_{-6}, T_{-5}, \ldots, T_0)$ are threshold measurements made on day i, and $(SM_{-6}, SM_{-5}, \ldots, SM_0)$ are calculates safety margins on day i, where $i = -6, -5, \ldots, 0)$ if the number of days is seven.

In some examples, the safety margin calculation circuit 925 is configured to trend one or both of the trend pacing stimulation energy thresholds that induce an evoked response and the calculated safety margins, such as over an extended period of time. The controller circuit 915 determines a pacing stimulation energy using a trended pacing stimulation energy threshold and a trended calculated safety margin. In some examples, the safety margin circuit is able to trend safety margins for the RV separately from safety margins for the LV. Information concerning the separate safety margins for the RV and LV may be useful to adjust cardiac resynchronization therapy (CRT). The trended information may be useful to a health care provider in adjusting or prescribing a drug therapy regimen for the patient. The trended information may also be an indication of modeling that is occurring for one or both ventricles.

In some examples, the device 900 includes a communication circuit 940 communicatively coupled to the controller circuit 915. The communication circuit 940 is configured to provide wireless communications with a second device. The controller circuit 915 may generate an alert associated with a calculated or trended safety margin. The alert is presented to a user by the second device.

According to some examples, the therapy circuit 910 may provide pacing stimulation energy to different combinations of electrodes, such as the electrodes described above in regard to FIG. 1. Because different combinations of electrodes may provide pacing stimulation in different directions, a combination of electrodes is sometimes called a pacing vector. Thus, the therapy circuit 910 may be able to deliver pacing stimulation energy to the heart using a plurality of pacing vectors. The controller circuit 915 may select a vector, or rank available vectors, for pacing according to some criterion such as impedance measurements or electrode location (e.g., a likelihood that using the pacing vector will stimulate the diaphragm or phrenic nerve). An approach for automatic vector detection can be found in Kwok et al, "Thoracic or Intracardiac Impedance Detection with Automatic Vector Detection," U.S. Pat. No. 7,630,763, filed Apr. 20, 2005, which is incorporated herein by reference in its entirety.

In some examples, the safety margin calculation circuit 925 calculates a safety margin for at least a portion of the plurality of the pacing vectors. The controller circuit 915 selects a pacing vector for delivering pacing stimulation energy using the calculated safety margins. In certain examples, the controller circuit 915 selects a pacing vector for one or more of the RV, LV, and RA.

To determine a vector for pacing, the controller circuit 915 identifies candidate pacing vectors for delivering pacing stimulation energy to a heart chamber. In some examples, the available vectors are indicated in memory that is programmed at the time of implant. In some examples, the controller circuit 915 enters a test mode and identifies available pacing vectors, such as by measured impedance. The controller circuit 915 delivers pacing stimulation energy to the heart using a plurality of the candidate pacing vectors.

The controller circuit 915 determines a pacing stimulation energy threshold that induces an evoked response for the portion of the identified candidate vectors, such as by initiating one or more threshold tests. The controller circuit 915 then calculates the safety margin and the pacing stimulation energy for a candidate vector using its calculated safety margin.

In some examples, the additional sensing circuit 930 includes a phrenic nerve activation (PNA) sensor to detect PNA. The PNA sensor may include an accelerometer or other motion sensor to detect a hiccup of the subject. The controller circuit 915 measures a phrenic nerve stimulation threshold for the portion of the identified candidate vectors and determines a difference between its measured phrenic nerve stimulation threshold and its calculated pacing stimulation energy.

The controller circuit 915 selects a pacing vector from among the candidate vectors according to the difference between its measured phrenic nerve stimulation threshold and its calculated pacing stimulation energy. It is desired to have the phrenic nerve stimulation as far as possible from the pacing stimulation energy to avoid unintended phrenic nerve stimulation.

Figure 10A:
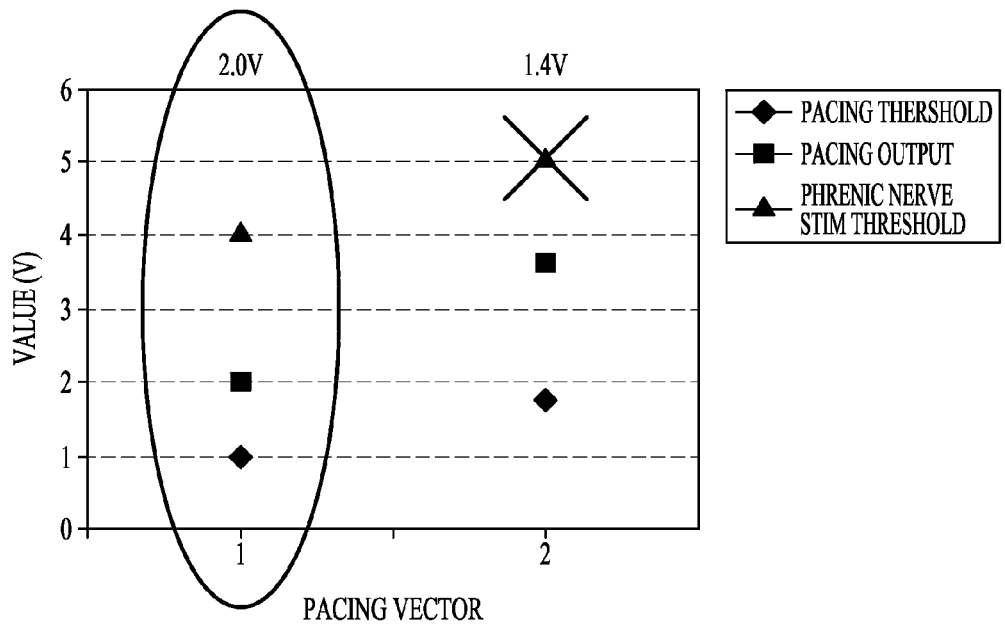
FIGS. 10A and 10B show examples of selecting between two pacing vectors.
Figure 10B:
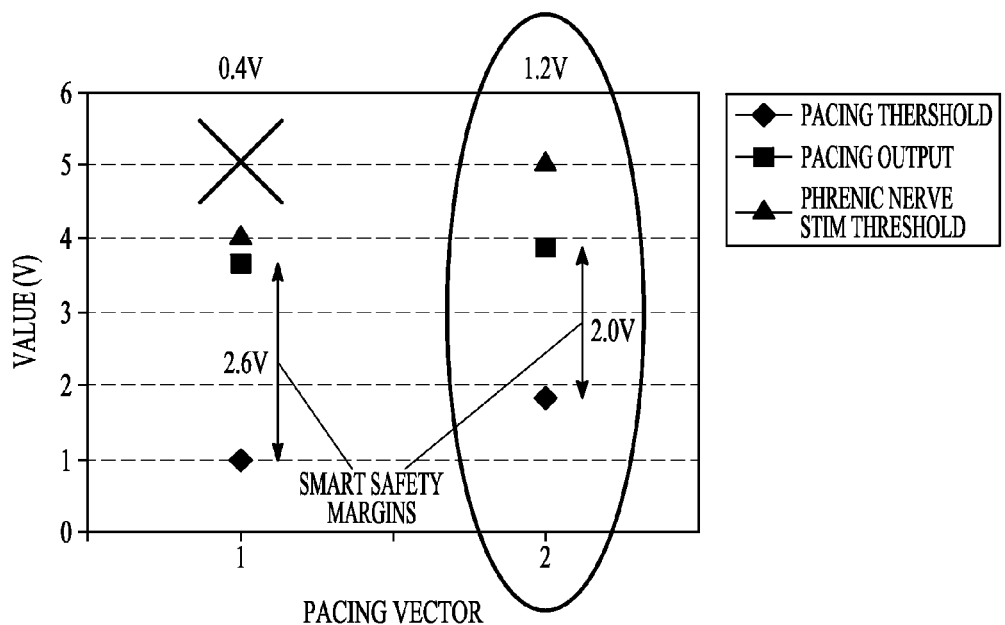

FIGS. 10A and 10B show two examples of selecting between two pacing vectors using the difference between the measured phrenic nerve stimulation threshold and the pacing stimulation energy. The example in FIG. 10A does not use a calculated optimized safety margin. Pacing Vector No. 1 would be chosen based on the difference between the phrenic nerve stimulation because the difference between the phrenic nerve stimulation threshold and the determined pacing output is greater for Pacing Vector No. 1.

The example in FIG. 10B uses a calculated optimized safety margin. Pacing Vector No. 2 would be chosen in this case because the difference between the phrenic nerve stimulation threshold and the calculated pacing output is greater for Pacing Vector No. 2 in this example.

In some examples, the controller circuit 915 may receive a measured parameter associated with hemodynamic function based of pacing for at least a portion of the identified candidate vectors. The controller circuit 915 may receive the measured parameter from the additional sensing circuit 930 or a separate dedicated hemodynamic function circuit 945. A non-exhaustive list of the hemodynamic parameter includes one or more of blood pressure, oxygen saturation of the blood, cardiac impedance, or a heart sound parameter such as amplitude or timing of one or more heart sounds.

The controller circuit 915 selects a preferred pacing vector from among the candidate vectors according to the measured hemodynamic function parameter for that vector and the according to the difference between its measured phrenic nerve stimulation threshold and the calculated pacing stimulation energy for the vector. In certain examples, the controller circuit weights the two measures (the measured hemodynamic function parameter and the difference in thresholds) differently when selecting a vector.

It can be seen from the above descriptions that a calculating an optimized safety margin can be a useful tool for a cardiac function management device. The optimized safety margin can improve automaticity of the device by enhancing automatic vector selection and can improve pacing therapy efficacy.

Additional Notes

The above detailed description includes references to the accompanying drawings, which form a part of the detailed description. The drawings show, by way of illustration, specific embodiments in which the invention can be practiced. These embodiments are also referred to herein as "examples."

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An apparatus comprising:
a cardiac signal sensing circuit configured to provide an electrical cardiac signal representative of cardiac activity of a subject;
a therapy circuit configured to deliver electrical pacing stimulation energy to a heart of the subject; and
a controller circuit communicatively coupled to the cardiac signal sensing circuit and the therapy circuit, and including a capture detection circuit configured to detect cardiac capture, wherein the controller circuit is configured to:
  initiate delivery of pacing stimulation energy to the heart using a first energy level;
  change the delivery of pacing stimulation energy level by at least one of: a) increasing the pacing stimulation energy from the first energy level until detecting that the pacing stimulation energy induces stable capture, or b) reducing the pacing stimulation energy from the first energy level until detecting that the pacing stimulation energy fails to induce the cardiac capture; and
  continue the changing of the pacing stimulation energy level until confirming the stable capture or the failure to induce the cardiac capture;
  wherein the controller circuit includes a safety margin calculation circuit configured to calculate a safety margin of pacing stimulation energy using at least one of:
    a determined stability of a parameter associated with evoked response; and
    a determined range of energy levels corresponding to intermittent failure to induce the cardiac capture, wherein the safety margin is indicative of a stimulation energy range between detected cardiac capture and stable cardiac capture, and
  wherein the controller circuit is configured to calculate a stimulation energy level for pacing therapy using the calculated safety margin and a stimulation energy level that induced cardiac capture.

2. The apparatus of claim 1,
wherein the controller circuit is configured to measure the parameter associated with the evoked response during the delivery of the pacing stimulation energy and induced cardiac capture, and
wherein the safety margin calculation circuit is configured to:
  categorize parameter measurements into specified ranges of parameter values;
  determine stability of the parameter associated with the evoked response by identifying a range of values that includes a largest number of parameter measurements;
  identify a smallest pacing stimulation energy that induced capture resulting in a measured parameter in the range of values that includes the largest number of parameter measurements; and
  calculate the safety margin using the smallest pacing stimulation energy.

3. The apparatus of claim 1,
wherein the controller circuit is configured to measure the parameter associated with the evoked response during delivery of the pacing stimulation energy and induced cardiac capture, and
wherein the safety margin calculation circuit is configured to:
  determine stability of the parameter associated with the evoked response by specifying a range of values of the parameter associated with the evoked response;
  identify a largest pacing stimulation energy resulting in a measured parameter value outside the specified range of values of the parameter associated with the evoked response; and
  calculate the safety margin using the largest pacing stimulation energy.

4. The apparatus of claim 1, wherein the parameter associated with the evoked response includes at least one of:
a peak amplitude of the evoked response;
a time between delivery of the pacing stimulation energy and occurrence of the peak amplitude of the evoked response;
a time between delivery of the pacing stimulation energy and occurrence of a zero-crossing of an amplitude of the evoked response;
a polarity of a detected T-wave associated with the evoked response;
a positive slope of a sensed cardiac signal that includes the evoked response; and
a negative slope of a sensed cardiac signal that includes the evoked response.

5. The apparatus of claim 1, including a cardiac impedance sensing circuit communicatively coupled to the controller circuit and configured to provide a signal representative of cardiac impedance, and wherein the parameter associated with the evoked response includes at least one of:
a near-DC value of a cardiac impedance signal;
a peak-to-peak amplitude of the cardiac impedance signal; and
a zero-to-peak amplitude of the cardiac impedance signal.

6. The apparatus of claim 1, including at least one of:
a heart sound sensor configured to provide a signal representative of mechanical activity of the heart; and
a pulmonary pressure sensor configured to provide a signal representative of pulmonary pressure, and
wherein parameter associated with the evoked response includes at least one of:
  a measured amplitude of a heart sound associated with the evoked response;
  a time of occurrence of the heart sound associated with the evoked response;
  a power of the heart sound associated with the evoked response; and
  pulmonary pressure.

7. The apparatus of claim 1, wherein the safety margin circuit is configured to:
calculate the safety margin using the determined range of energy levels corresponding to intermittent failure to induce the cardiac capture; and
when stimulation energy corresponding to the stable capture is different from the stimulation energy corresponding to confirmed cardiac capture, then calculate the safety margin as an energy level of the pacing stimulation energy corresponding to stable capture plus a specified stimulation energy increment value minus an energy level corresponding to confirmed cardiac capture,
otherwise use a specified minimum increment of the pacing stimulation energy as the safety margin.

8. The apparatus of claim 1, wherein the safety margin circuit is configured to:
   calculate the safety margin using a range of energy levels corresponding to intermittent failure to induce capture; and
   when a stimulation energy level corresponding to a confirmed loss of capture is different from a stimulation energy corresponding to a first detected loss of capture, then calculate the safety margin as a difference between an energy level immediately prior to first detecting loss of capture and an energy level immediately prior to confirming loss of capture,
   otherwise use a specified minimum increment of the pacing stimulation energy as the safety margin.

9. The apparatus of claim 1, including a memory circuit integral to or communicatively coupled to the controller circuit, and wherein the safety margin calculation circuit is configured to:
   trend pacing stimulation energy thresholds that induce an evoked response;
   trend calculated safety margins, and
   wherein the controller circuit is configured to determine a pacing stimulation energy using a trended pacing stimulation energy threshold and a trended calculated safety margin.

10. The apparatus of claim 1,
   wherein the therapy circuit is configured to deliver pacing stimulation energy to the heart using a plurality of pacing vectors,
   wherein the safety margin calculation circuit is configured to calculate the safety margin for at least a portion of the plurality of the pacing vectors, and
   wherein the controller circuit is configured to select a pacing vector for delivering pacing stimulation energy using the safety margins.

11. The apparatus of claim 10, wherein the controller circuit is configured to:
   identify candidate pacing vectors for delivering pacing stimulation energy to a heart chamber;
   receive a parameter measurement from a hemodynamic function circuit, wherein the parameter measurement indicates hemodynamic function of pacing for at least a portion of the candidate pacing vectors;
   determine a pacing stimulation energy threshold that induces an evoked response for the portion of the candidate pacing vectors;
   determine a phrenic nerve stimulation threshold for the portion of the candidate vectors;
   calculate a pacing stimulation energy for a candidate pacing vector using its calculated safety margin; and
   select a pacing vector from among the candidate pacing vectors according to its measured hemodynamic function parameter and a difference between its measured phrenic nerve stimulation threshold and its calculated pacing stimulation energy.

* * * * *